United States Patent [19]

Lee

[11] 4,360,413

[45] Nov. 23, 1982

[54] CREATINE KINASE ISOENZYME ELECTROPHORETIC TECHNIQUE AND IMPROVED CREATINE KINASE ISOENZYME REAGENT FOR USE THEREIN

[75] Inventor: Robert T. Y. Lee, Oceanside, Calif.

[73] Assignee: Beckman Instruments, Inc., Fullerton, Calif.

[21] Appl. No.: 284,871

[22] Filed: Jul. 20, 1981

Related U.S. Application Data

[63] Continuation of Ser. No. 221,096, Dec. 29, 1980, abandoned.

[51] Int. Cl.³ .............................................. G01N 27/00
[52] U.S. Cl. ................................................. 204/180 G
[58] Field of Search .................................... 204/180 G

[56] References Cited

U.S. PATENT DOCUMENTS

| | | | |
|---|---|---|---|
| 4,012,285 | 3/1977 | Pleiderer et al. | 195/103.5 R |
| 4,013,513 | 3/1977 | Lederer | 195/66 R |
| 4,036,697 | 7/1977 | Pierre et al. | 195/99 |
| 4,042,462 | 8/1977 | Johnson et al. | 195/103.5 R |
| 4,067,775 | 1/1978 | Wurzburg et al. | 195/99 |
| 4,097,336 | 6/1978 | Pierre et al. | 195/99 |
| 4,105,499 | 8/1978 | Kiyasu | 195/103.5 R |
| 4,162,194 | 7/1979 | Pierre et al. | 435/15 |
| 4,200,691 | 4/1980 | Buege et .l. | 435/17 |

*Primary Examiner*—Howard S. Williams
*Attorney, Agent, or Firm*—R. J. Steinmeyer; J. E. Vanderburgh; Robert S. Frieman

[57] ABSTRACT

A creatine kinase reagent of the type comprising a buffer, creatine phosphate, adenosine diphosphate, D-glucose, hexokinase, glucose-6-phosphate dehydrogenase, a thiol compound, magnesium ion, adenosine monophosphate, and a coenzyme selected from a group consisting of nicotinamide adenine dinucleotide, nicotinamide adenine dinucleotide phosphate, and mixtures thereof. The reagent is characterized in that it further comprises an effective amount of an enzyme selected from a group consisting of phosphogluconate dehydrogenase and phosphogluconate dehydrogenase (decarboxylating).

An electrophoretic technique for assaying the relative distribution of creatine kinase characterized in that the above reagent is employed therein.

15 Claims, No Drawings

CREATINE KINASE ISOENZYME ELECTROPHORETIC TECHNIQUE AND IMPROVED CREATINE KINASE ISOENZYME REAGENT FOR USE THEREIN

This is a continuation of application Ser. No. 221,096, filed Dec. 29, 1980, now abandoned.

BACKGROUND OF THE INVENTION

1. Field of the Invention

The instant invention pertains to an electrophoretic technique for measuring creatine kinase isoenzymes and to a creatine kinase isoenzyme reagent for use therein.

2. Description of the Prior Art

Electrophoretic and other methods for measuring creatine kinase and creatine kinase isoenzymes are known to those skilled in the art (1-8). Yasmineh et al. (8) report that the sensitivity obtained via electrophoretically separating and measuring the isoenzymes of creatine kinase is relatively lacking, especially when the activity of a creatine kinase isoenzyme is very low with respect to another, as is frequently the case with creatine kinase isoenzyme that originates from the heart (the "MB" isoenzyme) and is present in serum after myocardial damage.

Accordingly, it would be very desirable to increase the sensitivity obtained via the electrophoretic separation and measurement of the isoenzymes of creatine kinase without encumbering the convenient technique embodied in the present electrophoretic method.

SUMMARY OF THE INVENTION

In accordance with the present invention, there is provided an improved creatine kinase isoenzyme electrophoretic technique and an improved creatine kinase isoenzyme reagent wherein the sensitivity of the improved electrophoretic technique is increased 400%. More particularly, the improved electrophoretic technique of the instant invention for assaying the relative distribution of creatine kinase isoenzymes is of the type wherein a sample to be assayed is applied to an electrophoretic gel; the electrophoretic gel is electrophoresed; the electrophoresed, electrophoretic gel is contacted with a reagent to thereby produce a series of simultaneous reactions between the creatine kinase isoenzymes and the constituents of the reagent; and a product of the simultaneous reactions present in the resultant electrophoresed pattern is measured to determine the relative distribution of the creatine kinase in the assayed sample.

The simultaneous reactions employed in the present invention are of the type comprising: (a) reacting creatine phosphate with adenosine diphosphate in the presence of creatine kinase to form creatine and adenosine triphosphate; (b) reacting adenosine triphosphate with D-glucose in the presence of hexokinase to form adenosine diphosphate and glucose-6-phosphate; and (c) reacting glucose-6-phosphate with a coenzyme selected from a group consisting of nicotinamide adenine dinucleotide, nicotinamide adenine dinucleotide phosphate, and mixtures thereof in the presence of glucose-6-phosphate dehydrogenase to form 6-phosphogluconate and the reduced form of said coenzyme.

The creatine kinase reagent employed in the present invention is of the type comprising a buffer, creatine phosphate, adenosine diphosphate, D-glucose, hexokinase, glucose-6-phosphate dehydrogenase, a thiol compound, magnesium ion, adenosine monophosphate, and a coenzyme selected from a group consisting of nicotinamide adenine dinucleotide, nicotinamide adenine dinucleotide phosphate, and mixtures thereof.

Typical thiol compounds include, but are not limited to, dithioerythritol, dithiothreitol, mercaptoethanol, cysteine, and N-acetyl-L-cysteine.

The creatine kinase reagent of the instant invention is characterized in that it further comprises an effective amount of an enzyme selected from a group consisting of phosphogluconate dehydrogenase and phosphogluconate dehydrogenase (decarboxylating).

The use of this improved creatine kinase reagent in the electrophoretic technique of this invention results in a series of simultaneous reactions wherein the 6-phosphogluconate generated in reaction step (c) is reacted with the coenzyme in the presence of an enzyme selected from the group consisting of phosphogluconate dehydrogenase and phosphogluconate dehydrogenase (carboxylating) to thereby produce an additional mole of reduced coenzyme and, accordingly, increase the sensitivity of the creatine kinase electrophoretic technique.

An unexpected advantage of the instant invention is that although only an additional mole of the reduced coenzyme is produced, thereby doubling the amount of reduced coenzyme available for measurement, the sensitivity of the improved creatine kinase electrophoretic technique of the instant invention is increased four fold, i.e., an increase in sensitivity 200% greater than expected.

Still other features and attendant advantages of the present invention will become apparent to those skilled in the art from a reading of the following detailed description of the preferred embodiments.

DESCRIPTION OF THE PREFERRED EMBODIMENTS

The reagent employed in the creatine kinase isoenzyme electrophoretic technique of the instant invention preferably comprises a buffer having a pH of about 5.5 to about 7.5; at least about 5 mM creatine phosphate; at least about 1 mM adenosine diphosphate; at least about 5 mM D-glucose; at least about 3,000 IU/l hexokinase; at least about 3,000 IU/l-glucose-6-phosphate dehydrogenase; at least about 5 mM thiol compound; at least about 2 mM magnesium ion; up to 5 mM adenosine monophosphate; at least about 1 mM of the coenzyme; and at least about 500 IU/l of the enzyme.

More preferably, the reagent employed in the instant invention comprises a buffer having a pH of about 6 to about 7; from about 5 to about 20 mM creatine phosphate; from about 1 to about 7mM adenosine diphosphate; from about 5 to about 35 mM D-glucose; from about 3,000 to about 13,000 IU/l hexokinase; from about 3,000 to about 15,000 IU/l glucose-6-phosphate dehydrogenase; from about 5 mM to about 35 mM thiol compound; from about 2 to about 28 mM magnesium ions; from about 1 to about 5 mM adenosine monophosphte; from about 1 to about 7 mM of the coenzyme; and from about 500 to about 3,000 IU/l of the enzyme.

It is further preferred that the reagent employed in the instant invention comprise a buffer having a pH of about 6 to 7; about 15 mM creatine phosphate; from about 3 to about 4 mM adenosine disphosphate; about 20 mM D-glucose; from about 6,000 to about 7,500 IU/l glucose-6-phosphate dehydrogenase; from about 15 to about 20 mM thiol compound; from about 14 to about 19 mM magnesium ion; about 5 mM adenosine monophosphate; from about 2 to about 4 mM of the coenzyme; and about 1,500 IU/l phosphogluconate dehydrogenase (decarboxylating).

An optimal reagent for use in the creatine kinase isoenzyme electrophoretic technique of the instant invention comprises a buffer comprising 22 mM 3-(N-morpholino)-2-hydroxypropane sulfonic acid (MOPSO) buffer and 101 mM MOPSO buffer, sodium salt; about 15 mM creatine phosphate, disodium 4H$_2$O; about 4 mM adenosine diphosphate, trilithium XH$_2$O; about 20 mM D-glucose, anhydrous; about 6,500IU/l hexokinase; about 7,500 IU/l glucose-6-phosphate dehydrogenase; about 20 mM N-acetyl-L-cysteine; about 15 mM magnesium acetate; about 5 mM adenosine monophosphate, monohydrate; about 4 mM nicotinamide adenine dinucleotide phosphate, monosodium; and about 1,500 IU/l phosphogluconase dehydrogenase (decarboxylating).

If one desires to measure the creatine kinase isoenzyme pattern via a colorimetric technique, as opposed to a fluorometric technique, one would then employ a reagent which further comprises a compound capable of reacting with the reduced form of the coenzyme to produce a colored product capable of such colorimetric measurement. For example, a tetrazolium compound, e.g., iodonitrotetrazolium violet, 2,3,5-triphenyl tetrazolium chloride and [3-(4,5-dimethylthiazole-2-yl)-2,5-diphenyl-2N-tetrazolium bromide], can be included in the reagent. This tetrazolium compound can react with the reduced coenzyme to form a reduced colored dye. Alternatively, in the presence of diaphorase and/or phenazine methosulfate the reduced co-enzyme can react with the tetrazolium compound to form a reduced colored dye.

Electrophoretic techniques for separating creatine kinase are well known to those skilled in the art (7, 8) and, accordingly, need not be elaborated herein.

The following examples are provided for the purpose of further illustration only and are not intended to be limitations on the disclosed invention.

EXAMPLE 1

Within run precision and between run precision of a creatine kinase isoenzyme electrophoretic procedure within the scope of this invention was determined in conjunction with a creatine kinase isoenzyme reagent within the scope of this invention comprising creatine kinase, 15 mM; adenosine-5'-diphosphate (ADP), 4 mM; adenosine-5'-monophosphate (AMP), 5 mM; magnesium, 15 mM; D-glucose, 20 mM; nicotinamide adenine dinucleotide phosphate (NADP), 4 mM; N-acetyl-L-cysteine, 20 mM; hexokinase (yeast), 6,650 IU/l; glucose-6-phosphate dehydrogenase (yeast), 7,500 IU/l; and 6-phosphogluconate dehydrogenase (decarboxylating), 1,500 IU/l; and an MOPSO buffer comprising 5 grams 3(n-morpholino)-2-hydroxypropane sulfonic acid and 7.0 grams 3(n-mopholino)-2-hydroxypropane sulfonic acid-sodium salt, having a reconstituted pH of 7.0±0.1.

The within run precision was determined by performing 10 replicate analysis of the same specimen on 10 agarose gels and the between run precision was determined by replicate analysis of one specimen on 10 gels over a two day period. The results of these analyses are set forth in Table I.

TABLE I

| Gel # | $\bar{X}$ | SD | CV |
|---|---|---|---|
| A. Precision CK1 (Within-Run) | | | |
| 1 | 17.17 | 1.97 | 11.48 |
| 2 | 19.90 | 1.62 | 8.16 |
| 3 | 17.40 | 1.64 | 9.44 |
| 4 | 17.65 | 1.42 | 8.02 |
| 5 | 17.35 | 1.28 | 7.35 |
| 6 | 16.09 | 1.04 | 6.44 |
| 7 | 14.42 | 1.49 | 10.30 |
| 8 | 18.20 | 1.63 | 8.97 |
| 9 | 18.32 | 1.48 | 8.06 |
| 10 | 15.07 | 0.88 | 5.83 |
| Between-Run Precision CK2 | | | n = 10 |
| | $\bar{X}$ = 16.87 | SD = 1.51 | CV = 8.96 |
| B. Precision CK2 (Within-Run) | | | |
| 1 | 28.78 | 2.39 | 8.30 |
| 2 | 27.97 | 2.92 | 10.46 |
| 3 | 30.03 | 1.78 | 5.94 |
| 4 | 30.27 | 3.06 | 10.11 |
| 5 | 30.47 | 1.56 | 5.11 |
| 6 | 29.06 | 1.32 | 4.53 |
| 7 | 30.44 | 0.90 | 2.97 |
| 8 | 29.60 | 1.44 | 5.04 |
| 9 | 31.28 | 0.72 | 2.31 |
| 10 | 33.34 | 1.11 | 3.32 |
| Between-Run Precision CK2 | | | n = 10 |
| | $\bar{X}$ = 29.97 | SD = 2.84 | CV = 9.47 |
| C. Precision CK3 (Within-Run) | | | |
| 1 | 54.01 | 3.82 | 7.06 |
| 2 | 52.12 | 3.76 | 7.21 |
| 3 | 52.55 | 2.72 | 5.17 |
| 4 | 51.84 | 3.95 | 7.62 |
| 5 | 52.09 | 1.67 | 3.20 |
| 6 | 54.85 | 1.80 | 3.29 |
| 7 | 55.16 | 2.08 | 3.78 |
| 8 | 53.24 | 1.89 | 3.54 |
| 9 | 50.50 | 1.96 | 3.87 |
| 10 | 51.78 | 1.96 | 3.78 |
| Between-Run Precision | | | n = 10 |
| | $\bar{X}$ = 53.13 | SD = 3.20 | CV = 6.02 |

EXAMPLE 2

Studies were conducted by assaying ten levels of an elevated control serum. The control serum was diluted with denatured pooled serum to yield the dilutions shown in Table II.

| Dilution No. | Percent of Original Contrations |
|---|---|
| 1 | 100% |
| 2 | 93.8% |
| 3 | 72.8% |
| 4 | 56.8% |
| 5 | 49.2% |
| 6 | 29.5% |
| 7 | 24.8% |
| 8 | 12.5% |
| 9 | 8.3% |
| 10 | 3.2% |

A regression analysis was performed for each creatine kinase isoenzyme and results obtained therefrom are set forth in Table III.

TABLE III

| Parameters | Regression Analysis CK Isoenzyme | | |
|---|---|---|---|
| | CK 1 | CK 2 | CK 3 |
| Slope | 0.98669 | 3.92310 | 5.48409 |
| Intercept | 2.02354 | 3.85087 | 5.16720 |
| Std. Error | 3.32565 | 4.31516 | 3.29849 |
| $R^2$ | 0.98522 | 0.99890 | 0.99965 |
| N | 10 | 10 | 10 |

EXAMPLE 3

The creatine kinase isoenzyme reagent of Example 1 was submitted to comparative testing against the Beckman brand MAXIZONE TM rehydratable agarose gel. A regression analysis performed on the resulting data yielded the information set forth in Table IV.

TABLE IV

N = 146
Slope = 1.020
Intercept = 0.686
r = 0.997
r squared = 0.994

EXAMPLE 4

To demonstrate the improved sensitivity of a creatine kinase isoenzyme reagent and electrophoretic technique within the scope of this invention, a comparative assay was performed using the reagents set forth in Table V.

TABLE V

| Constituent | Reagent Within Scope of Invention | Reagent Outside Scope of Invention |
|---|---|---|
| Creatine Phosphate, Disodium 4H$_2$O, 15 mM | X | X |
| N—Acetyl-L-Cysteine, 20 mM | X | X |
| Adenosine Diphosphate, Trilithium XH$_2$O, 4 mM | X | X |
| Magnesium Acetate, 20 mM | X | X |
| D-Glucose, Anhydrous, 5 mM | X | X |
| Adenosine Monophosphate, Monohydrate, 5 mM | X | X |
| Nicotinamide Adenine Dinucleotide Phosphate, Monosodium, 4 mM | X | X |
| MOPSO Buffer, 22 mM | X | X |
| MOPSO Buffer, Sodium Salt, 101 mM | X | X |
| Hexokinase (lyophilized), 6650 IU/l | X | X |
| Glucose-6-Phosphate Dehydrogenase (lyophilized), 7500 IU/l | X | X |
| 6-Phosphoglucomate Dehydrogenase (lyophilized), 1500 IU/l | X | |

The comparative assay of this example employed the following protocol:

Protocol 1.0 Sample

A Dade brand creatine kinase isoenzyme control was titered in denatured pooled human serum containing less than 10 IU/l of CK$_3$.

2.0 Electrophoresis 2.1 The titered samples were applied to agar gels via template method.

2.2 The gels were electrophoresed for 20 minutes at 100 volts.

2.3 Each of the creatine kinase isoenzyme reagents of Table V was reconstituted with deionized water.

2.4 Each of the reconstituted creatine kinase isoenzyme reagents of Table V (2 ml) was applied to 3.25×4 inch sheets of filter paper. Each filter paper was applied to a gel surface.

2.5 The gels were incubated at 45° C. for 20 minutes.

2.6 The filter paper was removed and the gels were dried at 75° C.

2.7 Each gel was scanned on a fluorescence densitometer.

The results obtained via this comparative assay are set forth in Table VI.

TABLE VI

| Sample No. | Dilution Dade Control | Total IU/l | % CK$_3$ | % CK$_2$ | % CK$_1$ | IU/l CK$_3$ | IU/l CK$_2$ | IU/l CK$_1$ | Scan CK$_3$ | Peak CK$_2$ | Height CK$_1$ |
|---|---|---|---|---|---|---|---|---|---|---|---|
| Creatine Kinase Isoenzyme Reagent Within Scope of Invention (with 6PGDH) | | | | | | | | | | | |
| 1 | 1/3 | 1032 | 43.5 | 39.0 | 17.5 | 449 | 402 | 181 | 97 | 86 | 47 |
| 2 | 1/4 | 767 | 43.4 | 38.8 | 17.8 | 333 | 298 | 137 | 85 | 75 | 33 |
| 3 | 1/5 | 594 | 50.0 | 38.6 | 11.4 | 297 | 229 | 68 | 80 | 63 | 22 |
| 4 | 1/6 | 490 | 53.9 | 35.7 | 10.5 | 264 | 175 | 51 | 80 | 52 | 18 |
| 5 | 1/10 | 300 | 56.9 | 35.0 | 8.1 | 171 | 105 | 24 | 60 | 35 | 9 |
| 6 | 1/12 | 227 | 61.9 | 31.2 | 6.9 | 141 | 71 | 16 | 47 | 22 | 5 |
| 7 | 1/24 | 112 | 63.3 | 30.2 | 6.5 | 71 | 34 | 7.3 | 18 | 13 | 2.5 |
| 8 | 1/48 | 56 | 58.5 | 35.1 | 6.4 | 33 | 20 | 3.6 | 12 | 7 | 1.5 |
| 9 | 1/96 | 30 | 66.2 | 31.6 | 2.2 | 20 | 9.5 | 0.66 | 5 | 3 | 0.5 |
| 10 | 1/192 | 12 | | | | not detectable | | | | | |
| Creatine Kinase Isoenzyme Reagent Outside Scope of Invention (without 6PGDH) | | | | | | | | | | | |
| 11 | 1/3 | 1032 | 46.4 | 33.5 | 20.1 | 479 | 346 | 207 | 87 | 58 | 32 |
| 12 | 1/4 | 767 | 47.3 | 89.4 | 13.3 | 363 | 302 | 102 | 71 | 38 | 12 |
| 13 | 1/5 | 594 | 49.0 | 37.7 | 13.2 | 291 | 224 | 78 | 58 | 30 | 11 |
| 14 | 1/6 | 490 | 53.2 | 35.5 | 11.3 | 261 | 174 | 55 | 62 | 29 | 10 |
| 15 | 1/10 | 300 | 64.1 | 29.5 | 6.4 | 192 | 89 | 19 | 40 | 18 | 5 |
| 16 | 1/12 | 227 | 65.7 | 28.3 | 6.0 | 149 | 64 | 14 | 38 | 16 | 4 |
| 17 | 1/24 | 112 | 58.8 | 36.1 | 5.1 | 66 | 40 | 5.7 | 16 | 9 | 1.5 |
| 18 | 1/48 | 56 | | | | | not detectable | | | | |
| 19 | 1/96 | 30 | | | | | not detectable | | | | |

TABLE VI-continued

| Sample No. | Dilution Dade Control | Total IU/1 | % $CK_3$ | % $CK_2$ | % $CK_1$ | IU/1 $CK_3$ | IU/1 $CK_2$ | IU/1 $CK_1$ | Scan $CK_3$ | Peak $CK_2$ | Height $CK_1$ |
|---|---|---|---|---|---|---|---|---|---|---|---|
| 20 | 1.192 | 12 | | | | not detectable | | | | | |

As can be seen from Table VI, the creatine kinase isoenzyme reagent within the scope of this invention containing 6-phosphoglucomate dehydrogenase (decarboxylating) produces greater fluorescence than a similar reagent differing solely in the absence therefrom of the 6-phosphoglucomate dehydrogenase (decarboxylating). The minimum creatine kinase fraction detection level with the reagent containing 6-phosphoglucomate dehydrogenase (decarboxylating) is 0.66 IU as compared with 5.7 IU for a reagent devoid of 6-phosphoglucomate dehydrogenase (decarboxylating). Similarly, the minimum sample detection level with a reagent containing 6-phosphoglucomate dehydrogenase (decarboxylating) can have a 1/96 dilution as compared to the 1/24 dilution with a reagent devoid of 6-phosphoglucomate dehydrogenase (decarboxylating). Accordingly, since a reagent within the scope of this invention would theoretically only produce an additional mole of reduced coenzyme, one would expect that the minimum CK fraction detection level for a reagent within the scope of this invention would be one half of the detection level for a corresponding reagent devoid of the auxiliary enzyme. However, surprisingly it has been found that a reagent within the scope of this invention can detect a minimum creatine kinase fraction over eight times smaller than is detectable with the corresponding creatine kinase isoenzyme reagent devoid of the auxiliary enzyme (i.e., a detection level over four times lower than that theoretically expected). A comparison of the minimum sample dilution levels obtainable with a reagent within the scope of this invention to that obtainable with a corresponding reagent devoid of the auxiliary enzyme shows that one can still detect the creatine kinase isoenzymes in a sample 200% more dilute than theoretically expected.

Based on this disclosure, many other modifications and ramifications will naturally suggest themselves to those skilled in the art. These are intended to be comprehended as within the scope of this invention.

Bibliography

1. U.S. Pat. No. 4,012,285.
2. U.S. Pat. No. 4,013,513.
3. U.S. Pat. No. 4,042,462.
4. U.S. Pat. No. 4,067,775.
5. U.S. Pat. No. 4,105,499.
6. U.S. Pat. No. 4,200,691.
7. Roe et al., *J. Lab. Clin. Med.*, 80:577-590 (1972).
8. Yasmineh et al., *Clin. Chem.*, 21(3):381-386 (1975).

The embodiments of the invention in which an exclusive property or privilege is claimed are defined as follows:

1. A creatinine kinase reagent of the type comprising a buffer, creatinine phosphate, adenosine diphosphate, D-glucose, hexokinase, glucose-6-phosphate dehydrogenase, a thiol compound, magnesium ion, adenosine monophosphate, and a coenzyme selected from the group consisting of nicotinamide adenine dinucleotide, nicotinamide adenine dinucleotide phosphate and mixtures thereof, characterized in that said reagent further comprises an enzyme selected from a group consisting of phosphogluconate dehydrogenase and phosphogluconate dehydrogenase (decarboxylating) in an amount sufficient to react 6-phosphogluconate with said coenzyme in the presence of said enzyme.

2. The reagent of claim 1 comprising:
   (a) said buffer having a pH of about 5.5 to about 7.5;
   (b) at least about 5 mM creatine phosphate
   (c) at least about 1 mM adenosine diphosphate;
   (d) at least about 5 mM D-glucose;
   (e) at least about 3,000 IU/1 hexokinase;
   (f) at least about 3,000 IU/1 glucose-6-phosphate dehydrogenase;
   (g) at least about 5 mM thiol compound;
   (h) at least about 2 mM magnesium ion;
   (i) up to 5 mM adenosine monophosphate;
   (j) at least about 1 mM of said coenzyme; and
   (k) at least about 500 IU/1 of said enzyme.

3. The reagent of claim 1 comprising:
   (a) said buffer having a pH of about 6 to about 7;
   (b) from about 5 to about 20 mM creatine phosphate;
   (c) from about 1 to about 7 mM adenosine diphosphate;
   (d) from about 5 to about 35 mM D-glucose;
   (e) from about 3,000 to about 13,000 IU/1 hexokinase;
   (f) from about 3,000 to about 15,000 IU/1 glucose-6-phosphate dehydrogenase;
   (g) from about 5 mM to about 35 mM thiol compound;
   (h) from about 2 to about 28 mM magnesium ion;
   (i) from about 1 to about 5 mM adenosine monophosphate;
   (j) from about 1 to about 7 mM of said coenzyme; and
   (k) from about 500 to about 3,000 IU/1 of said enzyme.

4. The reagent of claim 1 comprising:
   (a) said buffer having a pH of about 6 to about 7;
   (b) about 15 mM creatine phosphate;
   (c) from about 3 to about 4 mM adenosine diphosphate;
   (d) about 20 mM D-glucose;
   (e) from 6,000 to about 7,500 IU/1 hexokinase;
   (f) from about 6,000 to about 7,500 IU/1 glucose-6-phosphate dehydrogenase;
   (g) from about 15 to about 20 mM thiol compound;
   (h) from about 14.7 to about 19.6 mM magnesium ion;
   (i) about 5 mM adenosine monophosphate;
   (j) from about 2 to about 4 mM of said coenzyme; and
   (k) about 1,500 IU/1 phosphogluconate dehydrogenase (decarboxylating).

5. The reagent of claim 1 comprising:
   (a) a buffer comprising 22 mM MOPSO buffer and 101 mM MOPSO buffer, sodium salt;
   (b) about 15 mM creatine phosphate, disodium $4H_2O$;
   (c) about 4 mM adenosine diphosphate, trilithium $XH_2O$;
   (d) about 20 mM D-glucose, anhydrous;
   (e) about 6,650 IU/1 hexokinase;
   (f) about 7,500 IU/1 glucose-6-phosphate dehydrogenase;
   (g) about 20 mM N-acetyl-L-cysteine;
   (h) about 15 mM magnesium acetate;
   (i) about 5 mM adenosine monophosphate, monohydrate;

(j) about 4 mM nicotinamide adenine dicleotide phosphate, monosodium; and (k) about 1,500 IU/l phosphogluconate dehydrogenase (decarboxylating).

6. The reagent of claim 1 further comprising a compound capable of reacting with the reduced form of said coenzyme to produce a colored product capable of being measured colorimetrically.

7. The reagent of claim 6 wherein said compound is a tetrazolium compound.

8. An improved electrophoretic technique for assaying the relative distribution of creatine kinase of the type wherein a sample to be assayed is applied to an electrophoretic gel, said electrophoretic gel is electrophoresed, said electrophoresed, electrophoretic gel is contacted with a reagent thereby producing a series of simultaneous reactions between the creatine kinase and the constituents of said reagent, said simultaneous reactions comprising:

(a) reacting creatine phosphate with adenosine diphosphate in the presence of creatine kinase to form creatine and adenosine triphosphate;

(b) reacting adenosine triphosphate with D-glucose in the presence of hexokinase to form adenosine diphosphate and glucose-6-phosphate; and (c) reacting glucose-6-phosphate with a coenzyme selected from a group consisting of nicotinamide adenine dinucleotide, nicotinamide adenine dinucleotide phosphate, and mixtures thereof in the presence of glucose-6-phosphate dehydrogenase to form 6-phosphogluconate and the reduced form of said coenzyme;

and measuring the reduced coenzyme present in the resulting electrophoresed pattern to determine the relative distribution of said creatine kinase in the assayed sample;

the electrophoretic technique being improved in that said 6-phosphogluconate is reacted with said coenzyme in the presence of an enzyme selected from a group consisting of phosphogluconate dehydrogenase and phosphogluconate dehydrogenase (decarboxylating) to produce an additional mole of said reduced coenzyme, thereby increasing the sensitivity of the creatine kinase electrophoretic technique.

9. The improved electrophoretic technique of claim 8 wherein said reagent comprises a buffer, creatine phosphate, adenosine diphosphate, D-glucose, hexokinase, glucose-6-phosphate dehydrogenase, a thiol compound, ion, adenosine monophosphate, a coenzyme selected from a group consisting of nicotinamide adenine dinucleotide, nicotinamide adenine dinucleotide phosphate, and mixtures thereof, and an effective amount of an enzyme selected from a group consisting of phosphogluconate dehydrogenase and phosphoglyconate dehydrogenase (decarboxylating).

10. The improved electrophoretic technique of claim 9 wherein said reagent comprises (a) said buffer having a pH of about 5.5 to about 7.5;

(b) at least about 5 mM creatine phosphate;

(c) at least about 1 mM adenosine diphosphate;

(d) at least about 5 mM D-glucose;

(e) at least about 3,000 IU/l hexakinase;

(f) at least about 3,000 IU/l glucose-6-phosphate dehydrogenase;

(g) at least about 5 mM a thiol compound;

(h) at least about 2mM magnesum ion;

(i) up to 5 mM adenosine monophosphate;

(j) at least about 1 mM of said coenzyme; and (k) at least about 500 IU/l of said enzyme.

11. The improved electrophoretic technique of claim 9 wherein said reagent comprises (a) said buffer having a pH of about 6 to about 7;

(b) from about 5 to about 20 mM creatine phosphate;

(c) from about 1 to about 7 mM adenosine diphosphate;

(d) from about 5 to about 35 mM D-glucose;

(e) from about 3,000 IU/l to about 13,300 IU/l hexokinase;

(f) from about 3,000 to about 15,000 IU/l glucose-6-phosphate dehydrogenase;

(g) from about 5 mM to about 35 mM thiol compound;

(h) from about 2 to about 28 mM magnesium ion;

(i) from about 1 to about 5 mM adenosine monophosphate;

(j) from about 1 to about 7 mM of said coenzyme; and (k) from about 500 to about 3,000 IU/l of said enzyme.

12. The improved electrophoretic technique of claim 9 wherein said reagent comprises (a) said buffer having a pH of about 6 to about 7;

(b) about 15 mM creatine phosphate;

(c) from about 3 to about 4 mM adenosine diphosphate;

(d) about 20 mM D-glucose;

(e) from 6,000 to about 7,500 IU/l hexokinase;

(f) from about 6,000 to about 7,500 IU/l glucose-6 phosphate dehydrogenase;

(g) from about 15 to about 20 mM thiol compound;

(h) from about 14.7 to about 19.6 mM magnesium ion;

(i) about 5 mM adenosine monophosphate;

(j) from about 2 to about 4 mM of said coenzyme; and (k) about 1,500 IU/l phosphogluconate dehydrogenase (decarboxylating).

13. The improved electrophoretic technique of claim 9 wherein said reagent comprises (a) a buffer comprising 22 mM MOPSO buffer and 101 mm MOPSO buffer, sodium salt;

(b) about 15 mM creatine phosphate, disodium 4H2O;

(c) about 4 mM adenosine diphosphate, lithium XH2O;

(d) about 20 mM D-glucose, anhydrous;

(e) about 6,650 IU/l hexokinase;

(f) about 7,500 IU/l glucose-6-phosphate dehydrogenase;

(g) about 20 mM N-acetyl-L-cysteine;

(h) about 15 mM magnesium acetate;

(i) about 5 mM adenosine monophosphate, monohydrate;

(j) about 4 mM nicotinamide adenine dinucleotide phosphate, monosodium; and (k) about 1,500 IU/l phosphogluconate dehydrogenase (decarboxylating).

14. The improved electrophoretic technique of claim 9 wherein said reagent further comprises a compound capable of reacting with the reduced form of said coenzyme to produce a colored product capable of being measured colorimetrically.

15. The improved electrophoretic technique of claim 14 wherein said compound is a tetrazolium compound.

* * * * *